United States Patent
Wolf et al.

(10) Patent No.: US 9,848,924 B2
(45) Date of Patent: Dec. 26, 2017

(54) BONE PLATE

(71) Applicant: DePuy SYNTHES PRODUCTS, INC., Raynham, MA (US)

(72) Inventors: Stefan Wolf, Flumenthal (CH); This Aebi, Grenchen (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 498 days.

(21) Appl. No.: 14/103,285

(22) Filed: Dec. 11, 2013

(65) Prior Publication Data

US 2015/0157373 A1  Jun. 11, 2015

(51) Int. Cl.
*A61B 17/80* (2006.01)

(52) U.S. Cl.
CPC .......... *A61B 17/80* (2013.01); *A61B 17/8057* (2013.01); *A61B 17/8061* (2013.01)

(58) Field of Classification Search
CPC .. A61B 17/80; A61B 17/8061; A61B 17/8057
See application file for complete search history.

(56) References Cited

U.S. PATENT DOCUMENTS

| | | | | |
|---|---|---|---|---|
| 5,002,544 A | * | 3/1991 | Klaue | A61B 17/80 606/280 |
| 5,015,248 A | * | 5/1991 | Burstein | A61B 17/68 606/297 |
| 5,022,544 A | | 6/1991 | Dundas et al. | |
| 5,733,287 A | * | 3/1998 | Tepic | A61B 17/80 606/280 |
| 6,623,486 B1 | * | 9/2003 | Weaver | A61B 17/8057 606/281 |
| 6,706,046 B2 | * | 3/2004 | Orbay | A61B 17/8061 606/291 |
| 7,128,744 B2 | * | 10/2006 | Weaver | A61B 17/8057 606/280 |
| 2002/0143338 A1 | * | 10/2002 | Orbay | A61B 17/68 606/287 |

(Continued)

FOREIGN PATENT DOCUMENTS

| | | |
|---|---|---|
| EP | 0 684 017 | 11/1995 |
| EP | 2 559 394 | 2/2013 |

(Continued)

*Primary Examiner* — Zade Coley
(74) *Attorney, Agent, or Firm* — Fay Kaplun & Marcin, LLP

(57) ABSTRACT

A bone plate includes a first surface which, when the bone plate is positioned over a bone, faces the bone, and a second surface opposing the first surface, the bone plate comprising an elongate shaft portion extending along a longitudinal axis of the bone plate and including a plurality of through holes extending therethrough from the first surface to the second surface to receive a bone anchor therethrough and a head portion extending from an end of the elongate shaft portion along a length smaller than a length of the elongate shaft portion, a width of the head between lateral walls connecting edges of the first and second surface being greater than a width of the shaft distance between the lateral walls, wherein the second surface includes a cavity extending between a first one of the plurality of through holes situated closest to the head portion and the head portion.

22 Claims, 5 Drawing Sheets

(56) References Cited

U.S. PATENT DOCUMENTS

| | | | |
|---|---|---|---|
| 2003/0083661 A1* | 5/2003 | Orbay | A61B 17/8061 606/62 |
| 2004/0097937 A1* | 5/2004 | Pike | A61B 17/8085 606/282 |
| 2004/0260295 A1* | 12/2004 | Orbay | A61B 17/68 606/86 B |
| 2005/0010226 A1* | 1/2005 | Grady, Jr. | A61B 17/746 606/281 |
| 2005/0015089 A1* | 1/2005 | Young | A61B 17/8014 606/915 |
| 2005/0080421 A1* | 4/2005 | Weaver | A61B 17/8057 606/282 |
| 2008/0140127 A1 | 6/2008 | Vasta et al. | |
| 2008/0140130 A1* | 6/2008 | Chan | A61B 17/1728 606/280 |
| 2009/0088767 A1* | 4/2009 | Leyden | A61B 17/1721 606/96 |
| 2010/0179599 A1* | 7/2010 | Derouet | A61B 17/1728 606/280 |
| 2010/0249850 A1* | 9/2010 | Cerynik | A61B 17/866 606/281 |
| 2011/0004252 A1* | 1/2011 | Velikov | A61B 17/80 606/280 |
| 2011/0295324 A1* | 12/2011 | Donley | A61B 17/8061 606/289 |
| 2013/0096629 A1* | 4/2013 | Rollinghoff | A61B 17/80 606/281 |
| 2013/0274745 A1* | 10/2013 | Kmiec, Jr. | A61B 17/72 606/62 |

FOREIGN PATENT DOCUMENTS

| | | | |
|---|---|---|---|
| WO | 2004/045389 | 6/2004 | |
| WO | 2012/050424 | 4/2012 | |
| WO | WO 2012050424 A1 * | 4/2012 | A61B 17/8061 |

* cited by examiner

BONE PLATE

FIELD OF THE INVENTION

The present invention relates to the field of surgical devices. Specifically, the invention relates to a bone plate for fixing bone segments, in particular, the proximal femur of a patient.

BACKGROUND

For stabilizing and fixing bone fractures it is known to employ bone plates which are fixed on the bone by means of suitable fastening elements such as, for example, bone screws, along with pins, bolts or other bone anchors. To guarantee a secure fixation of the bone fragments to each other and of the bone plate on the bone, it is required that the bone anchors are incorporated into the bone precisely and so as to be adapted to the anatomy.

However, a bone plate attached to a bone is subject to mechanical loads, in particular a bending load. This load acts particularly on the weakest regions of a bone plate, namely those regions where through holes are provided. In particular, an elongate bone-plate shaft portion that is provided with through holes along its length has an irregular moment-of-resistance curve along its length and, upon excessive load, will be most likely to break in the region of a through hole, or at least be deformed in the region of a through hole, which would impede the introduction of a bone anchor through the through hole. For example, in a bone plate for the proximal femur comprising an elongate shaft portion and a head portion that is shorter and wider in comparison thereto, an especially high load occurs in the region of the through hole that is closest to the head portion, so that the risk of breakage is highest here. The object of the present invention is to provide a bone plate having a reduced risk of breakage upon a bending load on the bone plate.

SUMMARY OF THE INVENTION

According to a first aspect of the invention, the bone plate includes a first surface which, when the bone plate is positioned over a bone, faces the bone, and a second surface opposing the first surface so that when the bone plate is positioned over the bone, faces away from the bone. The bone plate comprises an elongate shaft portion including two lateral side walls which extend longitudinally relative to the bone plate to connect edges of the first and second surfaces, and a head portion that is shorter (i.e., a length of the head portion is smaller than a length of the shaft portion) and wider (i.e., a distance between opposing side walls of the head portion is greater than a distance between the side walls of the shaft portion) in comparison thereto. In the shaft portion a plurality of through holes extend through the bone plate from the first to the second surface, each of which are configured to receive a bone anchor. In an exemplary embodiment, the second surface facing away from the bone may have a cavity or indentation which extends between a one of the through holes situated closest to the head portion, (e.g., a first through hole along the shaft portion), and the head portion. In one exemplary embodiment, the cavity may extend into the head portion.

As explained at the outset, the risk of breakage upon a bending load on the bone plate is greatest in the region of the first through hole. Through the provision of the cavity in a region of the non-bone-facing second surface of the bone plate in which region the head portion passes into the shaft portion, (i.e., in the region of the plate between the head portion and the first through hole), the bone plate is weakened in a targeted manner. In other words, the flexibility of the bone plate is increased in this region to relieve stress in the region of the first through hole and reduce the risk of breakage in this region.

According to another aspect, the second surface facing away from the bone has a depression which overlaps the through hole situated closest to the head portion. In one exemplary embodiment, the depression may surround at least a portion of the through hole. This depression preferably serves to reduce stress peaks upon a bending load on the bone plate in the region of the through hole. In an exemplary embodiment, the cavity and the depression border on each other and pass into each other. In other words, the cavity and the depression are open to one another. In a further exemplary embodiment, the cavity and the depression have the same dimension in a transverse direction of the bone plate at a place where they border on each other (i.e., where the cavity and the depression meet). This simplifies the production of the cavity and the depression so that the cavity and the depression may be created in a single step during manufacturing, and avoids stress peaks in a transition region. In a plan view, an end of the cavity facing the head portion may have a rounded shape.

According to one exemplary embodiment, the cavity possesses a greater dimension in a longitudinal direction of the bone plate than in a transverse direction of the bone plate. Through the elongate shape, a greater region between the first through hole and the head portion can be spanned by the cavity. In one exemplary embodiment, the cavity is spaced from the longitudinal extending side walls of the bone plate. In other words, the cavity does not extend completely in a transverse direction of the bone plate between the two side edges, but rather the full thickness (i.e., a distance between the first and second surfaces) of the bone plate is retained proximate the side walls so as not to excessively weaken the bone plate in this region.

According to one exemplary embodiment, the cavity has a curved cross-sectional profile in a direction from the shaft portion to the head portion. Preferably, a depth of the cavity increases continuously in a direction from the shaft portion to the head portion and decreases continuously after a deepest point is reached. Thus, the cavity preferably does not have a planar bottom surface, but rather a bulged shape. The deepest point of the cavity can be located, for example, approximately in the middle of the cavity. In a further exemplary embodiment, the cavity may taper as it extends toward the head portion so that an edge of the cavity is preferably formed as smoothly as possible in the direction of the head portion. For example, the cavity may form an angle smaller than 20° with respect to the second surface and, preferably smaller than 15°, particularly preferably smaller than 10°.

A depth of the cavity can be chosen based on a geometry of the bone plate so as to optimize the curve of the bending load on the bone plate. In one exemplary embodiment, the depth of the cavity amounts to up to 15% of a thickness of the bone plate, preferably up to 20%, most preferably up to 30%, of the thickness of the bone plate. The thickness of the bone plate is defined here by a cross-sectional profile, cutting the through hole, of the bone plate in a transverse direction of the bone plate between the first and second surfaces. In other words, the thickness of the bone plate is defined as a distance between the first and second surfaces.

According to a further aspect of the invention, the bone plate again has a first, surface which, when the plate is positioned over the bone, faces the bone, and a second surface opposing the first surface to face away from the bone when the plate is positioned over the bone. The bone plate comprises an elongate shaft portion with two longitudinally extending side walls connecting edges of the first and second surfaces to define a width of the shaft portion (i.e., a distance between the two side walls), as well as a head portion that is shorter and wider in comparison thereto. In the shaft portion, according to this further aspect of the invention, a plurality of through holes extend through the bone plate from the first to the second surface, which are configured to respectively receive a bone anchor.

In one exemplary embodiment, the first, bone-facing surface may have recesses which extend from the opposing side surfaces over a part of the width of the shaft portion transversely to the direction of longitudinal extension of the shaft portion, each of the plurality of through holes having a plurality of recesses associated therewith, of which at least two, preferably three and, where applicable, all, recesses differ from each other and which respectively form a group of recesses, these groups of recesses being identical for each of the plurality of through holes.

Through the special arrangement of the recesses it is achieved that a bending load is distributed uniformly along the length of the shaft portion, so that a region in which a through hole is arranged does not constitute the weakest region, which, as explained at the outset, could lead to a deformation of the through hole or even to a breakage of the bone plate in the region of the through hole. Through the provision of different recesses which, respectively grouped, are associated with one of the through holes, the distribution of the bending load can be improved in comparison to identical recesses distributed over the shaft.

According to one exemplary embodiment, each group of recesses comprises a first, second and third recess which are arranged side by side in the longitudinal direction of the bone plate, the second recess lying between the first and third recesses and being formed smaller than the first and third recesses. On other words, the smaller second recesses may have, in a plan view, a smaller dimension in at least one direction than the first and third recesses. For example, the second recess may extend a smaller distance from one of the longitudinally extending side walls of the bone plate toward a center axis of the bone plate than the first and third recesses, e.g., the second recess is shorter, and/or has a smaller dimension along the side surface, i.e. In another exemplary embodiment, the second recess may be flatter than the first and third recesses (e.g., the second recess may have a smaller depth than the first and third recesses).

In a further exemplary embodiment, each group comprises a fourth recess which is different from the other three recesses and connects the second recess to the first or third recess. The fourth recess may have a substantially quadrangular shape and is flatter (e.g., has a smaller depth) and shorter (e.g., extends a smaller distance from one of the longitudinal side walls toward the center of the bone plate) than the first, second and third recesses.

According to a further exemplary embodiment, the groups of recesses are arranged offset from each other on the opposing side surfaces of the bone plate along the longitudinal direction of the bone plate, i.e. two groups of recesses do not lie opposite each other directly on the opposing side surfaces. Preferably, the groups of recesses extend alternately from the opposing side surfaces. Thus, the distances between the groups on the respective side surfaces are not too great. Preferably, two groups of recesses following each other in the direction of longitudinal extension of the shaft portion lie opposite each other on the opposing side surfaces. However the longitudinal extensions of the two group of recesses intersect, i.e. before one group of recesses ends in the direction of longitudinal extension of the shaft portion, another group of recesses already begins on the opposing side edge. It is preferable here that recesses of mutually opposing groups of recesses do not pass into each other. But it is not excluded that individual—not all—recesses of a group of recesses and recesses of the opposing side surfaces may extend into each other. Preferably, the through holes are arranged offset from each other alternately with regard to a center axis of the bone plate extending in the direction of longitudinal extension of the shaft portion. In particular, a group of recesses on one side of the center axis can then be associated with a through hole that lies closer, with regard to the center axis, to the side edge of the shaft portion opposing the group of recesses.

According to a further exemplary embodiment, the recesses extend from the side surfaces at most up to a center axis of the bone plate extending in the direction of longitudinal extension of the shaft portion. In particular, it is advantageous when the recesses do not extend over the total width of the bone plate. Thus, the bone plate is not excessively weakened.

According to a further exemplary embodiment, the bone plate has a head portion which is shorter and wider than the shaft portion, with the through holes and the recesses being arranged in the shaft portion. A cross-sectional area of the shaft portion transversely to the direction of longitudinal extension of the shaft portion is substantially constant along the longitudinal direction. In other words, a distance between side walls of the bone plate and a distance between the first and second surfaces of the bone plate are constant along a length of the shaft portion of the bone plate. The size and arrangement of the recesses correspond a distance between the through holes and the side walls, i.e. the more material of the bone plate is already lacking in a cross section due to a through hole, the smaller a recess is in this cross section, and vice versa.

In another exemplary embodiment, the shaft portion possesses along the direction of longitudinal extension of the shaft portion a substantially constant section modulus, in particular bending section modulus, in the direction of longitudinal extension. In particular, the cross-sectional area of the shaft portion along its longitudinal extension is preferably so adapted that the section modulus is constant, whereby the calculation of the section modulus includes the area moment of inertia of the cross-sectional area.

It will be appreciated that the section modulus can be subject to fluctuations due to slight deviations in the cross section or in the material, and is possibly not completely constant over the total length of the shaft portion. However, there is preferably obtained at least a uniform section modulus, i.e. the section modulus changes along the direction of the longitudinal extension of the shaft portion by at most 30%, preferably at most 20%, particularly preferably at most 10%.

In one exemplary embodiment, the recesses have their maximum depth along the longitudinally extending side surfaces. In a further exemplary embodiment, at least a respective one—and preferably all—of the recesses in the groups of recesses possess a depth that decreases from the corresponding side surface in the direction of a center axis of the bone plate extending in the direction of longitudinal extension of the shaft portion. It is advantageous when the recesses taper off as flatly as possible in the direction of the center axis, i.e. preferably enclose with the first surface an angle up to at most 2°, further preferably up to at most 15°, most preferably up to at most 10°.

According to one exemplary embodiment, the through holes are formed as combination holes and have a variable-angle hole portion and a compression hole overlapping therewith. The variable-angle portion has an inner surface with a thread-like structure which is interrupted by recesses and preferably tapers in the direction of the first surface. This enables an advantageous locking of a head locking screw with a head thread in the through hole. The compression hole is formed elongately in the direction of longitudinal extension of the shaft portion and possesses an unthreaded inner surface tapering in the direction of the first, bone-facing surface. The compression hole is preferably configured to receive a compression screw having a smooth screw head, the screw head sliding on the tapering inner surface of the compression hole, while the screws are being screwed in, causing a compression of the bone fracture as would be understood by one of ordinary skill in the art.

BRIEF DESCRIPTION OF THE DRAWINGS

The preceding summary of the invention as well as the following description of an exemplary embodiment will become more easily understandable in the light of the attached drawings. An exemplary embodiment of the invention will be described hereinafter with reference to the accompanying drawings. It will be appreciated, however, that the application is not limited to the exemplary embodiment shown.

DETAILED DESCRIPTION

Figure 1:
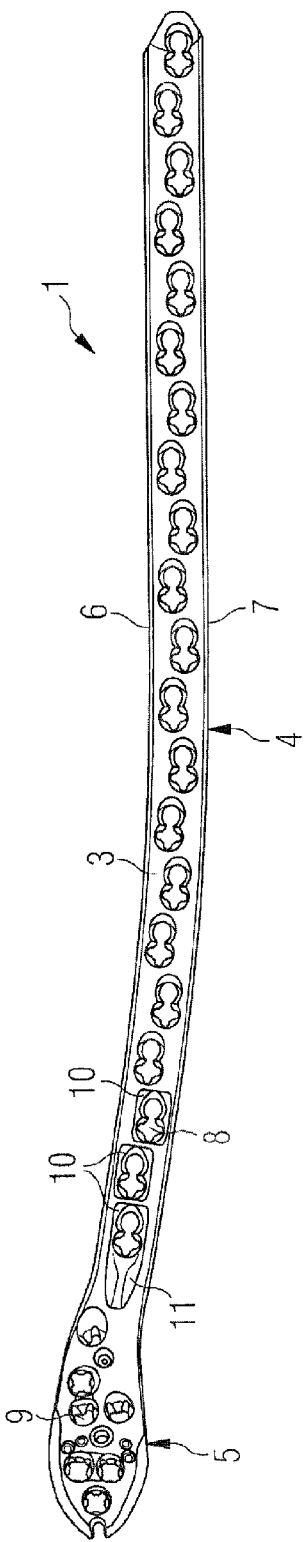
FIG. 1 shows a top plan view of a bone plate, according to an exemplary embodiment of the present invention.

The present invention may be further understood with reference to the following description and the appended drawings, wherein like elements are referred to with the same reference numerals. Exemplary embodiments of the present invention describe a bone plate for fixing fractures. In particular, the exemplary embodiments describes a bone plate including a depression extending through the bone plate and surrounding a through hole extending therethrough to reduce stress peaks, for example, along a portion of the between a through hole and a lateral side wall of the bone plate. Although the exemplary embodiments specifically describe a bone plate configured for the fixation of a proximal femur, it will be understood by those of skill in the art that the bone plate of the present invention may be adapted for the fixation of any of a variety of bones and, in particular, load bearing long bones.

Figure 2:
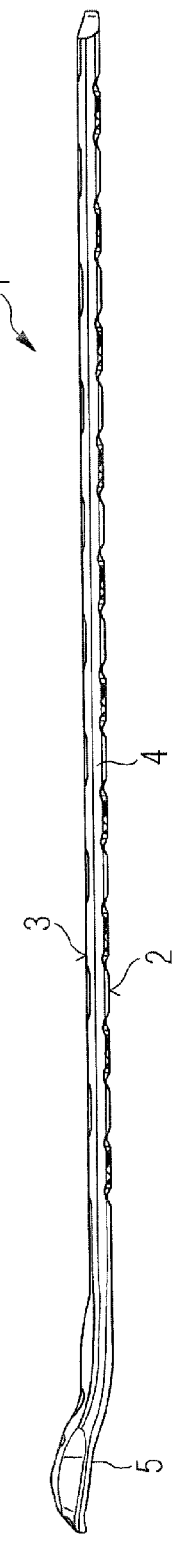
FIG. 2 shows a side view of the bone plate of FIG. 1.
Figure 3:
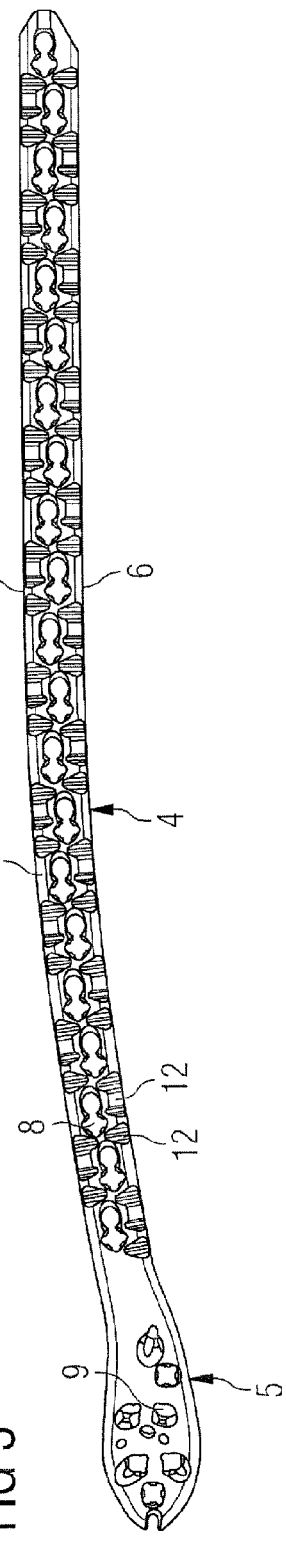
FIG. 3 shows a bottom plan view of the bone plate of FIG. 1.

FIG. 1 shows an exemplary embodiment of a bone plate 1 in plan view from an upper side—i.e., a first surface 3 of the bone plate 1 which, when the bone plate is implanted or positioned over a bone, faces away from the bone. The represented bone plate 1 is dimensioned for treating fractures of the left proximal femur, for example, of a human patient. It will be appreciated that the concepts described hereinafter are also applicable to other bone plates, in particular to a bone plate for the right proximal femur, the distal femur, or for other long bones, such as, for example, the tibia. In FIG. 2, the bone plate 1 is represented in a side view. FIG. 3 shows the bone plate 1 from an underside of the plate, i.e., from a second surface 2 which, when the bone plate is implanted or positioned over a bone, faces the bone.

Figure 4:
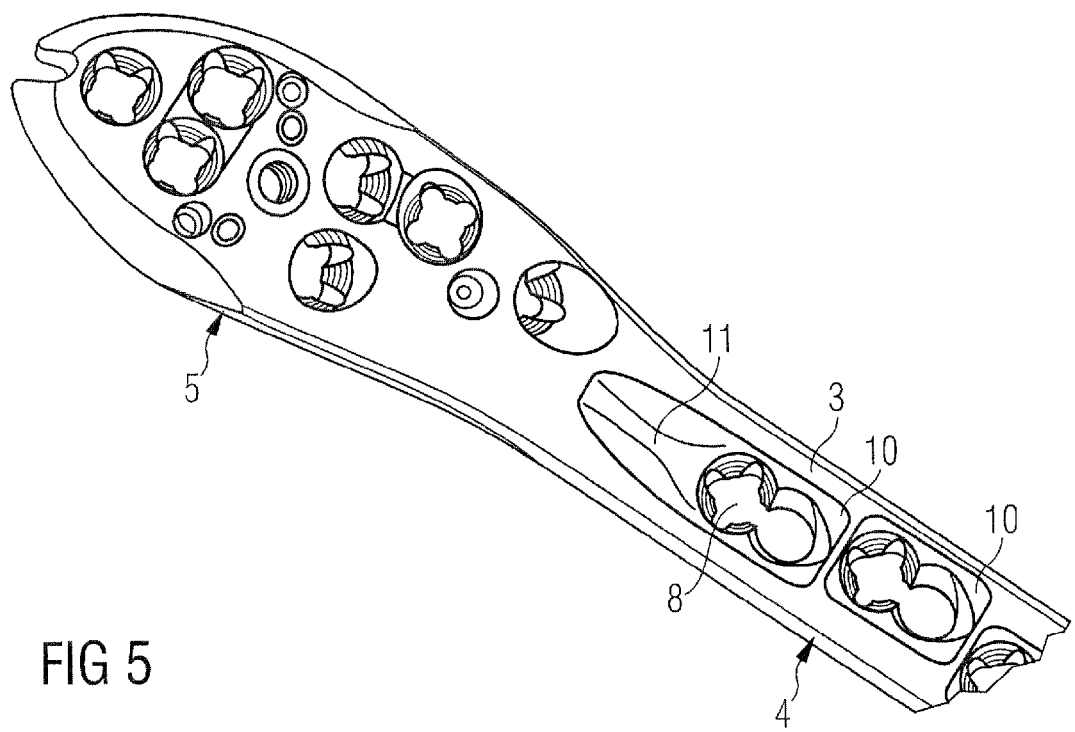
FIG. 4 shows a perspective view of a portion of the bone plate of FIG. 1.
Figure 5:
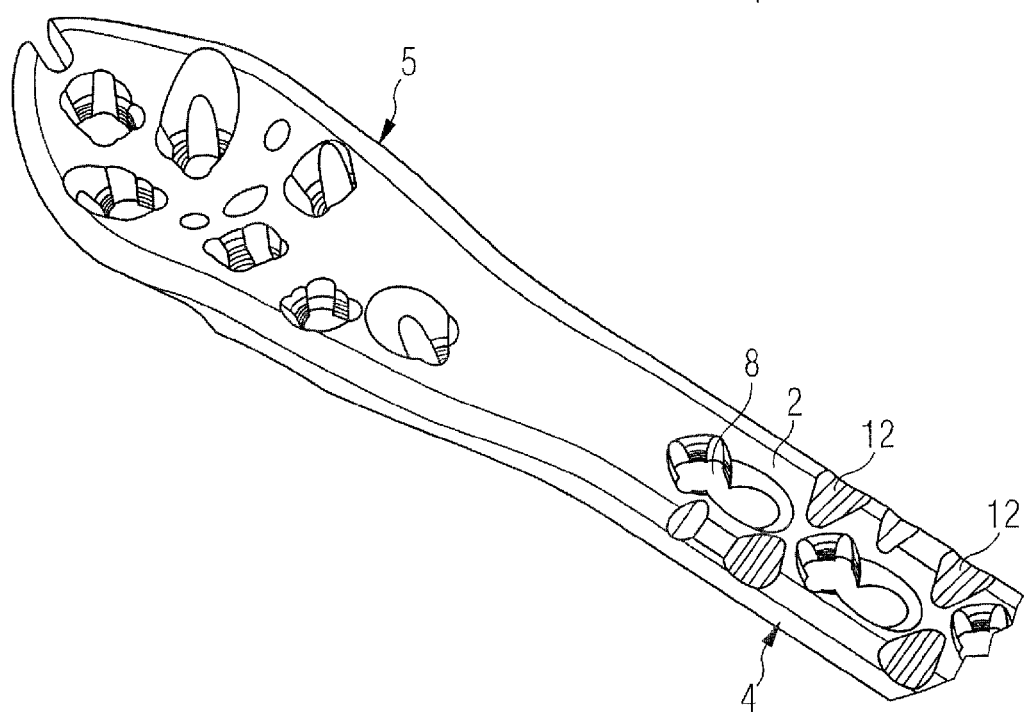
FIG. 5 shows a perspective view of a portion of the bone plate of FIG. 1.

The bone plate 1 comprises an elongate shaft portion 4 and a head portion 5 along with lateral side walls 6, 7 extending along the shaft portion 4 between the surfaces 2, 3 to define a width of the shaft portion 4. The width of the shaft portion 4 is substantially constant over a total length of the shaft portion 4. The head portion 5 is wider than the shaft portion 4, i.e., a distance between the surfaces 2, 3 is larger at the head portion 5 than at the shaft portion 4, and shorter than the shaft portion 4, i.e., a length of the head portion 5 along a longitudinal axis of the bone plate 1 is smaller than a length of the shaft portion 4 along the longitudinal axis of the bone plate. In one exemplary embodiment, the head portion 5 is preferably configured to adjoin the proximal femur, in particular, the greater trochanter. For example, the head portion 5 may have a curvature corresponding to the greater trochanter, as seen especially well in FIG. 2. The head portion 5 has a plurality of through holes 9, which may be formed here as variable-angle through holes and/or fixed angle through holes. In one exemplary embodiment, the head portion 5 may include, for example, seven through holes 9, three of which may be fixed angle through holes and the remaining through holes formed as variable angle through holes. It will be understood by those of skill in the art, however, that the plurality of through holes 9 may include any combination of variable angle and fixed angled through holes. The head portion 5 is also represented in FIGS. 4 and 5. FIG. 4 shows the head portion 5 in a perspective view from the first surface 3 of the bone plate 1, whereas FIG. 5 shows the head portion 5 of the bone plate 1 in a perspective view from the second surface 2 of the bone plate 1. The shaft portion 4 has an elongate shape and may include a slight curvature to correspond to the shape of the femur. It will be understood by those of skill in the art that a bone plate configured for the right proximal femur may have an accordingly opposite curvature.

The shaft portion 4 includes a plurality of through holes 8 along its length. The through holes 8 are preferably distributed uniformly along a longitudinal extension of the shaft portion 4. Preferably, the through holes 8 are arranged alternately offset from each other with respect to a center axis extending along the shaft portion 4, as seen in particular in FIGS. 1 and 3. The offset arrangement of the through holes 8 in offset manner reduces the risk of the subjacent bone splitting while bone screws are being screwed into the through holes 8.

Figure 8:
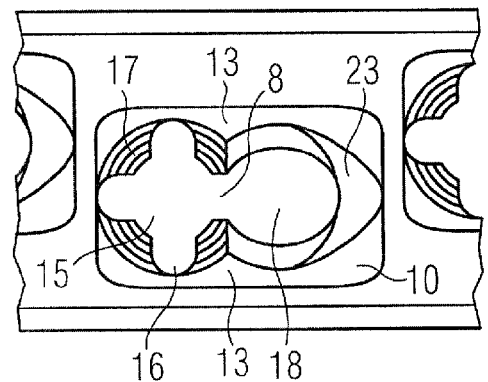
FIG. 8 shows a top plan view of a through hole extending through the bone plate of FIG. 1.

As represented in detail in FIG. 8, the through holes 8 in the shaft portion 4 are formed as combination holes. The through holes 8 have a variable-angle portion 15 as well as a compression hole 18. The variable-angle portion 15 possesses a rib- or thread-like structure 17 along an inner surface thereof, which tapers in a direction extending toward the bone-facing surface 2. The thread-like structure 17 is interrupted by recesses 16, which extend from the hole axis 19 radially outward. In the exemplary embodiment shown, there are formed four "columns" of the rib- or thread-like structure 17 which are separated from one another by the recesses 16. It will be understood by those of skill in the art, however, that the variable-angle portion 15 is not required to include four columns and may include, for example, 2 or more columns. As is known to the person skilled in the art, the variable-angle portion 15 is configured to receive a head locking screw which is introducible with its head thread into the variable-angle portion 15 of the through hole 8 at different angles, and lockable so that the screw is locked therewithin at a desired angle relative to the hole axis. The compression hole 18 has an unthreaded, i.e. smooth, inner surface 23 tapering in the direction of the bone-facing surface 2. The compression hole 18 is moreover elongated in the longitudinal direction of the shaft portion 4, so that the introduction of a compression screw with a smooth screw head therein causes a compression of the subjacent bone segments, as is known to the person skilled in the art.

As is represented in FIG. 1, the first three through holes 8 along the shaft 4 that are closest in distance to the head portion 5, respectively overlap a depression 10 on the surface 3 of the plate's upper side. In other words, the depression 10 may extend through a portion of the bone plate 1 surrounding, or at least partially surrounding, the through hole 8. Although the exemplary embodiment specifically shows and describes three through holes 8 as including a depression 10 extending thereabout, it will be understood by those of skill in the art that any number of the through holes 8 may include a depression 10 extending thereabout. Furthermore, there is provided on the plate's upper side in the surface 3 a cavity 11 between the first through hole 8—i.e., the through hole 8 closest in distance to the head portion 5—and the head portion 5. On the second surface 2 there are arranged, as represented in FIG. 3, groups of recesses 12 along the length of the shaft portion 4. The depressions 10 and the cavity 11 are likewise represented in FIGS. 4 and 6. The recesses 12 are seen in detail in FIGS. 5 and 7. The depressions 10, the cavity 11 and the recesses 12 contribute both individually and in combination to reducing the risk of breakage of the bone plate 1, as described in detail hereinafter. Hence, it will be appreciated that the depressions 10, the cavity 11 and the recesses 12 can be provided in a bone plate separately or together.

Figure 9:
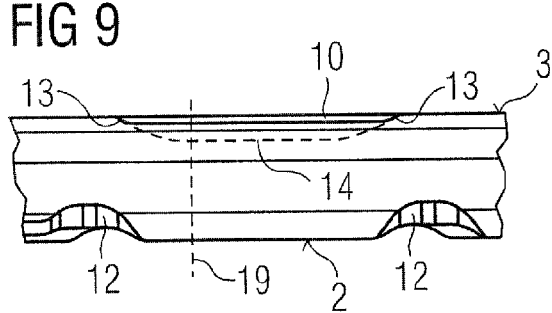
FIG. 9 shows a side view of the bone plate of FIG. 1, in the region of the through hole.
Figure 10:
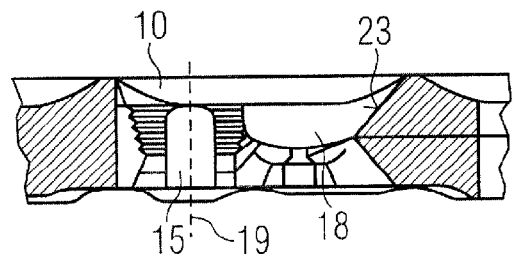
FIG. 10 shows a cross-sectional view of the bone plate of FIG. 1 along the line A-A in FIG. 6.

FIG. 8 shows the depression 10 in plan view of the plate's first surface 3. The depression 10 may have a substantially rectangular shape and completely overlaps the through hole 8 formed as a combination hole. In particular in the region of the recesses 16 of the variable-angle portion 15 of the through hole 8, which point in the direction of the lateral side walls 6, 7 of the shaft portion 4 of the bone plate 1, the provision of the depression 10 can reduce stress peaks that occur when a bending load or torsional load is imposed on the bone plate 1. The mouth of the through hole 8 is brought closer to a center plane of the bone plate 1 by the depression 10. The depression 10 can be produced, for example, by milling the surface 3 of the bone plate 1. The depression 10 has edge regions 13 which, in the represented embodiment, overlap with the recesses 16 which point in the direction of the side walls 6, 7. In FIG. 9 the depression 10 is represented in a side view of the bone plate 1. A bottom portion 14 (e.g., a portion defining a depth of the depression 10) is indicated by dashed lines. The bottom portion 14 is substantially planar, whereas edge regions 13 are curved. The edge regions 13 pass into the bottom region 14 smoothly. FIG. 10 shows a cross-section of the through hole 8 and the depression 10 in a section along the line A-A in FIG. 6. FIG. 10 also shows the variable-angle portion 15 which overlaps with the compression hole 18.

Figure 6:
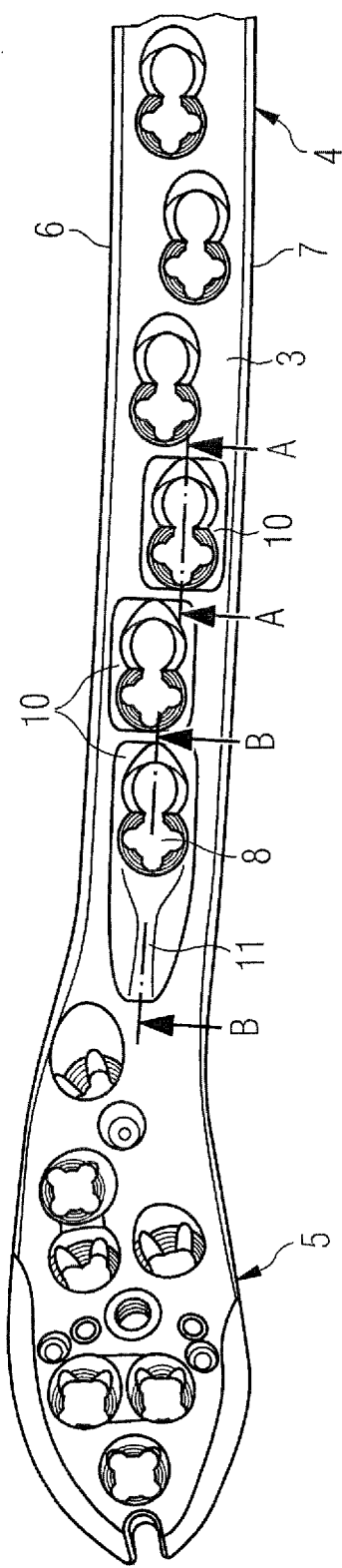
FIG. 6 shows an enlarged detailed view of the bone plate of FIG. 1.
Figure 11:
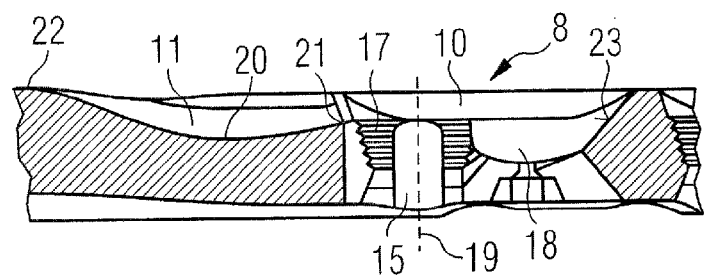
FIG. 11 shows a cross-sectional view of the bone plate of FIG. 1 along the line B-B in FIG. 6.

In FIG. 11 shows a cross-section of the bone plate 1 along the line B-B in FIG. 6. The sectional representation shows the first through hole 8, closest in distance to the head portion 5, which overlaps with the depression 10. As also represented in FIG. 6, the cavity 11 borders with its distal end 21 on the depression 10 of the first through hole 8. The depression 10 and the cavity 11 are open to one another at the end 21 of the cavity 11. The depression 10 and the cavity 11 may have the same width, in particular, at the place where they border on each other. This enables the cavity 11 and the depression 10 to be produced, for example milled, in one step. The cavity 11 serves to increase the flexibility in the region between the first through hole 8 and the head portion 5 of the bone plate 1, so as to reduce the risk of breakage of the bone plate in the region of the first through hole 8. In particular, the bone fracture can lie in the region of the bone plate 1 that lies between the first through hole 8 and the head portion 5, so that an especially high load acts on the bone plate 1 here.

As represented in FIG. 11, the cavity 11 has a curved cross-sectional profile. The depth of the cavity 11 increases continuously from the shaft portion 4 in the direction of the head portion 5 from the distal end 21 of the cavity 11 to a deepest point 20. From the deepest point 20 to a proximal end 22 of the cavity 11 the depth of the cavity 11 decreases continuously, with the cavity 11 tapering off relatively flat, that is to say, enclosing an angle, which in one embodiment, is smaller than 10° relative to the first surface 3 of the bone plate 1. As seen in FIGS. 4 and 6, the cavity 11 does not extend over the total width of the shaft portion 4 of the bone plate 1 (i.e., a distance between the lateral side walls 6, 7 of the bone plate), but is spaced from the side walls 6, 7. This retains a sufficient stability of the bone plate 1 in spite of the elevated flexibility caused by the cavity 11. The thicker edge regions absorb a greater part of a force flux than the bone plate 1 in the region of the cavity 11, so that the force flux is conducted around the first through hole 8 better than if the cavity 11 extended over the total width of the bone plate 1.

Figure 7:
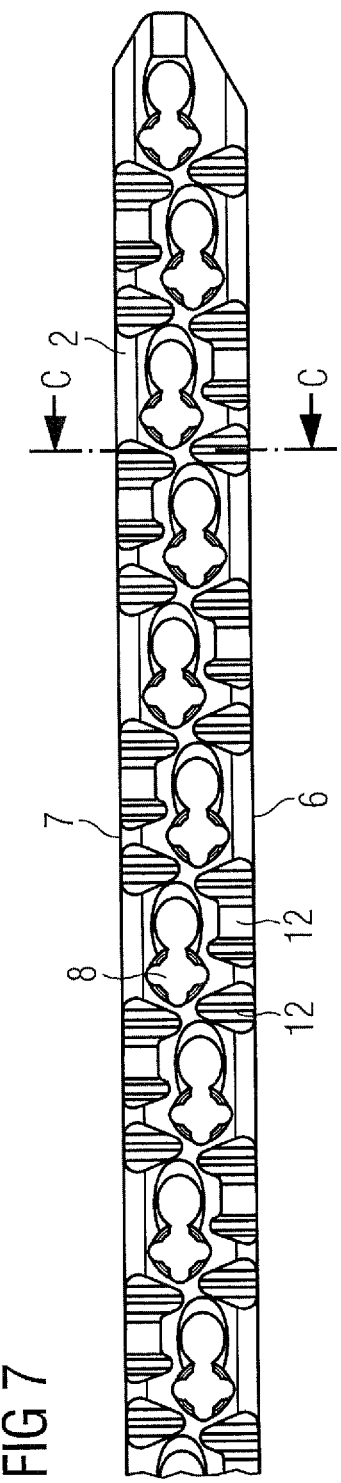
FIG. 7 shows an enlarged detailed view of the bone plate of FIG. 3.
Figure 12:
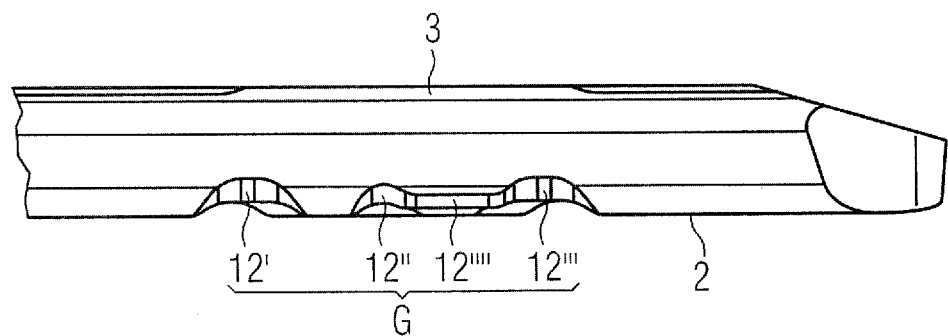
FIG. 12 shows a side view of a portion of the bone plate of FIG. 1.
Figure 13:
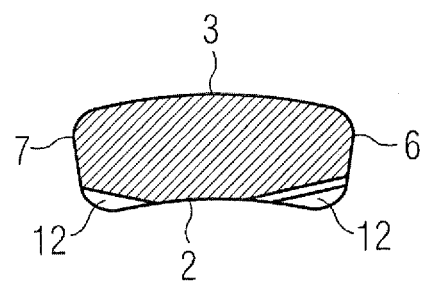
FIG. 13 shows a cross-sectional view of the shaft portion of the bone plate of FIG. 1, along the line C-C in FIG. 7.
Figure 14:
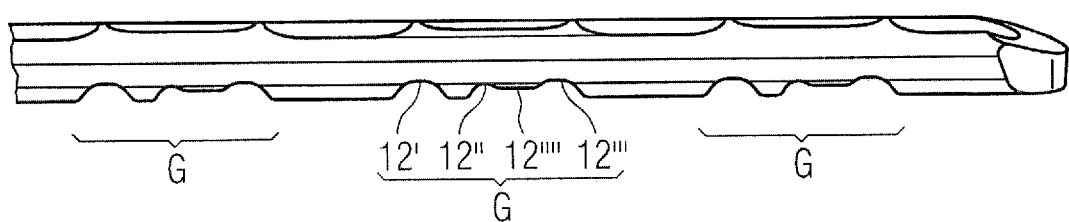
FIG. 14 shows a side view of the bone plate of FIG. 1, rotated by 10°.

In FIG. 12 there is represented a side view of the bone plate 1, in particular of the shaft portion 4, in which a group G of recesses 12 is to be seen. For the sake of better representability, FIG. 14 shows the shaft portion 4 in a view rotated by 10° about the longitudinal axis of the bone plate 1. FIG. 13 shows a cross-sectional view of the shaft portion 4 of the bone plate 1 along the line C-C in FIG. 7. As seen in FIGS. 7, 12 and 13, a group G of recesses 12 which is associated with one of the through holes 8 comprises four recesses 12', 12", 12''', 12'''', whereby in this embodiment not only a plurality, but all groups G have the identical four recesses 12', 12", 12''', 12'''' (except the first and the last group). In one exemplary embodiment, the first recess 12' and third recess 12''' are formed substantially identically, the second recess 12" being formed smaller. The fourth recess 12'''' connects the second and the third recess 12", 12''', so that these can alternatively also be regarded as a contiguous recess. As seen in FIG. 14, the recesses 12 extend from one of the side walls 6, 7 obliquely toward the center of the bone plate 1, having the greatest depth on the side wall 6, 7 of the bone plate 1. As seen in particular in FIG. 7, the groups G of recesses 12 are arranged alternately offset from each other on the opposing side walls 6, 7 of the shaft portion 4 of the bone plate 1 and in the direction of longitudinal extension of the shaft portion 4, with the opposing groups G of recesses 12 partly overlapping in the direction of longitudinal extension of the shaft portion 4. The arrangement of the groups G of recesses 12 corresponds to the arrangement of the through holes 8 along the longitudinal extension of the shaft portion 4. As seen in FIG. 7, the through holes 8 are arranged offset from each other alternately with respect to a center axis extending in the direction of longitudinal extension of the shaft portion 4. Accordingly, the groups G of recesses 12 are also arranged offset from each other alternately with regard to the center axis. Preferably, the cross-sectional area can respectively be formed along the longitudinal extension of the shaft portion 4 such that the section modulus of the shaft portion 4 is substantially constant along its longitudinal extension, but at least uniform, i.e. not subject to any great fluctuations. This avoids the highest stress upon a bending of the bone plate 1 occurring at a through hole 8. As seen in FIGS. 5 and 7, it will be appreciated that although the groups G of recesses 12 are preferably identical along the longitudinal extension of the shaft portion 4, the recesses 12 associated with the first through hole 8 (i.e., the through hole closest to the head portion 5) and the last through hole 8 (i.e., the through hole furthest from the head portion 5) are associated with a group G of recesses 12 which may not include all of the recesses 12', 12", 12''' and 12'''' described above, because the respective end of the shaft portion 4 is reached.

Although the preferred embodiment was described with reference to a left or right proximal femur, it will be appreciated that the principle of the invention can also be applied to bone plates for other bones. For example, the invention can also be employed for the distal femur, the tibia or other load bearing long bones. It will be appreciated that the shape and dimensioning of the bone plate can be adapted in accordance with the case of application without impairing the principle of the invention.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A bone plate having a first surface which, when the bone plate is positioned over a bone, faces the bone, and a second surface opposing the first surface, the bone plate comprising:
   an elongate shaft portion extending along a longitudinal axis of the bone plate and including a plurality of through holes extending therethrough from the first surface to the second surface configured to threadedly engage a bone screw therethrough;
   a head portion extending from an end of the elongate shaft portion along a length smaller than a length of the elongate shaft portion, a width of the head between lateral walls connecting edges of the first and second surface being greater than a width of the shaft between the lateral walls,
   wherein the second surface includes a cavity extending between a first one of the plurality of through holes situated closest to the head portion and the head portion, the cavity forming a contiguous concavity into the second surface, and
   wherein the bone plate has a thickness defined by a distance between the first and second surfaces of the bone plate, wherein the cavity extends into the second surface to a depth of no more than 30% of the thickness of the bone plate.

2. The bone plate according to claim 1, wherein the cavity extends into the head portion.

3. The bone plate according to claim 1, wherein the second surface includes a depression overlapping the first through hole, the cavity and the depression being open to one another.

4. The bone plate according to claim 3, wherein a width in a direction transverse to the longitudinal axis of the bone plate of a portion of the cavity bordering the depression is equal to a width in a direction transverse to the longitudinal axis of the bone plate of a portion of the depression bordering the cavity.

5. The bone plate according claim 1, wherein a length of the cavity in a longitudinal direction of the bone plate is greater than a width of the cavity in a direction transverse to the longitudinal axis of the bone plate.

6. The bone plate according to claim 1, wherein the cavity is spaced from the side walls of the bone plate.

7. The bone plate according to claim 1, wherein an end of the cavity extending toward the head portion is rounded.

8. The bone plate according to claim 1, wherein the cavity has a curved cross-sectional profile in a direction from the shaft portion to the head portion.

9. The bone plate according to claim 1, wherein the cavity has a depth that increases continuously in a direction from the shaft portion to the head portion to a deepest point and decreases continuously from the deepest point to an end of the cavity nearest the head portion.

10. The bone plate according to claim 1, wherein a depth of the cavity tapers in a direction toward the head portion.

11. A bone plate having a first surface which, when the bone plate is positioned over a bone, faces the bone, and a second surface opposing the first surface, the bone plate, comprising:
   an elongate shaft portion extending along a longitudinal axis of the bone plate and including two opposing side walls extending longitudinally between the first and second surfaces to connect edges thereof and define a width of the shaft portion;
   a plurality of first through holes extending through the bone plate from the first surface to the second surface, each of the first through holes being configured to receive a bone anchor therein; and
   a plurality of recesses in the first surface extending from the opposing side walls over a portion of the width of the shaft portion transverse to a longitudinal axis of the shaft portion, each of the first through holes having an identical group of recesses associated therewith, each group of recesses including a first recess and a second recess differing from one another,
   wherein each group of recesses includes a third recess, the first, second and third recesses of each group being arranged side by side in a direction along the longitudinal axis of the bone plate, the second recess of each group lying between the first and third recesses and having a dimension smaller than a dimension of the corresponding first and third recesses.

12. The bone plate according to claim 11, wherein each group includes a fourth recess interconnecting the second recess with one of the corresponding first and third recesses.

13. The bone plate according to claim 11, wherein the groups of recesses are offset from each other on the opposing side walls of the bone plate along a length of the bone plate.

14. The bone plate according to claim 11, wherein the groups of recesses extend alternately from the opposing side walls along a length of the bone plate.

15. The bone plate according to claim 14, wherein a portion of a first group of recesses extending from a first one of the opposing side walls lies directly across the bone plate from a portion of a second group of recesses immediately following the first group along a length of the bone plate.

16. The bone plate according to claim 11, wherein the recesses extend from the side walls at most up to a mid point of the bone plate between the opposing side walls.

17. The bone plate according to claim 11, wherein the bone plate includes a head portion extending from an end of the shaft portion along a length smaller than a length of the shaft portion, a width of the head portion being greater than a width of the shaft portion, the first through holes and the recesses being arranged in the shaft portion.

18. The bone plate according to claim 17, wherein a distance between the side walls of the shaft portion and a distance between the first and second surfaces is substantially constant along the shaft portion.

19. The bone plate according to claim 17, wherein a section modulus of the shaft portion is substantially constant long the longitudinal axis.

20. The bone plate according to claim 11, wherein a depth of the recesses is largest along the side walls.

21. The bone plate according to claim 11, wherein a depth of at least one of the recesses in each group of recesses decreases from a corresponding side wall toward a center axis of the bone plate extending in the direction of longitudinal extension of the shaft portion.

22. The bone plate according to claim 11, wherein each of the first through holes is a combination hole including a variable-angle portion having an inner surface with a thread-like structure interrupted by a plurality of gaps and a compression hole overlapping with the variable-angle portion, the compression hole being elongated in along the longitudinal axis and having an unthreaded inner surface tapering toward the first surface.

* * * * *

UNITED STATES PATENT AND TRADEMARK OFFICE
CERTIFICATE OF CORRECTION

PATENT NO.         : 9,848,924 B2
APPLICATION NO.    : 14/103285
DATED              : December 26, 2017
INVENTOR(S)        : Wolf et al.

Page 1 of 1

It is certified that error appears in the above-identified patent and that said Letters Patent is hereby corrected as shown below:

In the Claims

Claim 19, Column 12, Line 9:
"long the longitudinal axis." should read "along the longitudinal axis."

Signed and Sealed this
Twenty-eighth Day of May, 2019

Andrei Iancu
*Director of the United States Patent and Trademark Office*